United States Patent [19]

Bailey et al.

[11] 4,158,093
[45] Jun. 12, 1979

[54] PROCESS FOR SUBSTITUTING AND DEQUATERNIZING PYRIDYLETHYL QUATERNARY SALTS OF PYRIDINE AND BYPYRIDINE BASES

[75] Inventors: Thomas D. Bailey; Charles K. McGill, both of Indianapolis, Ind.

[73] Assignee: Reilly Tar & Chemical Corporation, Indianapolis, Ind.

[21] Appl. No.: 860,787

[22] Filed: Dec. 15, 1977

[51] Int. Cl.$^2$ ................ C07D 213/06; C07D 213/22; C07D 403/02
[52] U.S. Cl. .................................... 542/455; 546/193; 546/257; 546/258; 546/286; 546/290; 546/301; 546/304
[58] Field of Search .......... 260/296 R, 293.69, 290 R, 260/294.9, 294.8 G, 297 R; 542/455

[56] References Cited

U.S. PATENT DOCUMENTS

| 2,512,789 | 6/1950 | Cislak et al. | 260/290 |
|---|---|---|---|
| 2,742,463 | 4/1956 | Finkelstein | 542/455 |
| 3,049,547 | 8/1962 | Cislak | 260/294.8 |

OTHER PUBLICATIONS

Phillips, J. Org. Chem. vol. 14, pp. 302 to 305 (1949).
Kosower et al., J. Am. Chem. Soc., vol. 86, pp. 5524 to 5527 (1964).
Klingsberg, Pyridine and Its Derivatives, Part Two, pp. 24–25, Interscience Publishers Inc. NY (1961).
Klingsberg, Pyridine and Its Derivatives, vol. 12, chapter VII, pp. 368–369.
Baker et al., J. Org. Chem., vol. 20, pp. 118 to 134 (1955).
Berg et al., J. Org. Chem., vol. 41, pp. 2621 to 2624 (1976).
Aumann et al., J. Chem. Soc. Chem. Comm. 1973, pp. 32–33.
Ho et al., J. Am. Chem. Soc., vol. 79, abst. no. 78261m (1973).
Kutney et al., Synth. Commun., vol. 5, pp. 119–124 (1975).

Primary Examiner—John D. Randolph
Attorney, Agent, or Firm—Woodard, Weikart, Emhardt & Naughton

[57] ABSTRACT

A process for dequaternizing a 2-(2-pyridyl)ethyl or 2-(4-pyridyl)ethyl quaternary salt of a pyridine or bipyridine base comprising the step of heating or reacting the pyridylethyl quaternary salt with a caustic material such as sodium hydroxide. Also included is a process for preparing a second pyridine base (or a bipyridine base) in which a first pyridine base is initially selected and its 2-(2-pyridyl)ethyl or 2-(4-pyridyl)ethyl quaternary salt or its acid salt prepared. An electrophilic, nucleophilic or coupling reaction can then be performed on the quaternary salt to change the substituent or to form the bipyridyl coupling and the resultant salt dequaternized with a caustic material, such as sodium hydroxide, to produce a second pyridine or a bipyridine base.

81 Claims, No Drawings

PROCESS FOR SUBSTITUTING AND DEQUATERNIZING PYRIDYLETHYL QUATERNARY SALTS OF PYRIDINE AND BYPYRIDINE BASES

BACKGROUND OF THE INVENTION

This invention relates to the field of pyridine and its derivatives and, particularly, to a process for dequaternizing pyridylethyl quaternary salts of substituted pyridine and bipyridine bases.

Pyridine, its characteristic formula being $C_5H_5N$, has been long recognized as the parent ring system of a large number of naturally occuring products and important industrial, pharmaceutical and agricultural chemicals. It is an aromatic compound and, much like benzene, gives rise to a large number of substituted homologs and derivatives, many of which are found in the light- and middle-oil fractions of coal tar and are commonly known and referred to as pyridine bases. Bipyridyl compounds, generally categorized by their 2,2'-, 3,3'- and 4,4'- connections, are one such specific group of pyridine homologs and derivatives and have themselves been generally known to the art for many years.

In industrial applications, it is often desirable to transform or change one substituted pyridine base to a second substituted pyridine base either because of the greater availability of the first or because of the critical need of the second base for a given application. Known means for attempting such a transfer include both electrophilic and nucleophilic substitution reactions in addition to the coupling reaction which produces a bipyridyl, or bipyridine, base from an initial substituted pyridine base. It has long been known to the art, however, that such transformation or change is often not feasible or practicable with the pyridine base in its free state.

In this regard, it has likewise long been known that both electrophilic and nucleophilic substituent transformation or change can be readily performed on the quaternary salts of a great majority of such pyridine bases. For example, in the area of electrophilic condensation, or substitution, 2- and 4-alkylpyridines containing alpha hydrogens undergo condensations with carbonyl compounds to give alcohols which in some cases react further to produce unsaturated compounds. The formation of 2- and 4- ethanolpyridines is an important example of this reaction in which the usual reaction conditions require high temperatures whether in the gas phase or under high pressure. The picolines have been shown to react in like fashion with aromatic aldehydes to give stilbazoles. Thus, when 2-picoline is heated with benzaldehyde in the presence of zinc chloride at 200° C. for about 16 hours, 76% of the stilbazole is formed. See C. Williams, et al., *J. Org. Chem.*, v. 28, 387 (1963). The corresponding alkylpyridinium quaternary salts, on the other hand, react under much milder conditions as, for example, when 2-picoline methiodide in methanol was condensed at about 15° C. with benzaldehyde, using piperidine as the catalyst, to produce 73% of the stilbazole quaternary salt. See Philips, *J. Org. Chem.*, v. 12, 333 (1947).

In like fashion, the quaternary salts of alkylpyridines have been shown to react with ketones, esters, nitriles, anhydrides, alkylhalides and arylhalides in the presence of a weak base while the free pyridine bases require a strong alkali metal derivative such as sodamide. It is believed the hydrogens on the carbon alpha to the pyridine ring are more easily removed by mild organic bases such as secondary and tertiary amines in the case of the quaternary salts to produce anhydrobases which act as enamines and can be condensed with a number of electrophiles. Thus, the anhydrobase of 2-picoline methiodide condenses readily with acid chlorides, isocyanates, alkylhalides and carbon disulfide. Compare *Klingsberg*, v. 12, Chapter VII with Baker & McEvoy, *J. Org. Chem.*, v. 20, 118 (1955). Also, compare Weiss & Hauser, *J. Am. Chem. Soc.*, v. 71, 2026 (1949) with Adamcik & Flores, *J. Org. Chem.*, v. 29, 572 (1964) regarding the Michael additions of alkylpyridines and their quaternary salts.

Similar conclusions have been reached with regard to the comparison of nucleophilic substitution of various substituted pyridine bases with their quaternary salts. For example, it is reported that the relative rates of reaction of 2-chloropyridine and 1-methyl-2-chloropyridinium iodide with sodium methoxide in methanol at 50° C. are $3.3 \times 10^{-4}$ and $1.5 \times 10^5$, respectively, thereby illustrating that a quaternary salt can react $5 \times 10^8$ times faster than the corresponding free pyridine base. See Liveris & Miller, *J. Chem. Soc.*, 3486 (1963).

In addition, halopyridinium salts readily undergo nucleophilic amination at room temperature or at slightly elevated temperatures in refluxing methanol in harsh contrast to the rather rigorous conditions required for amination of corresponding free 2- and 4-halopyridine bases. Compare Haack, *Ger. Off.* 595, 361 C.A. 28:4069 (1934) and Michaelis & Millman, *Ann.*, v. 354, 91 (1907) with Wilbaut & Brockman, *Rec. Trav. Chim.*, v. 80, 309 (1961) and Hauser & Weiss, *J. Org. Chem.*, v. 14, 310 (1949). Comparison of the replacement reaction of thiopyridine analogs with their quaternary salts gives similar results [compare Schmidt & Giessilman, *Ber.*, vol. 93, 1590 (1960) with King & Ozoz, *J. Org. Chem.*, vol. 20, 448 (1955)], much as the cyano analogs [Poziomek, *J. Org. Chem.*, vol. 28, 590 (1963)] and the hydroxylation reaction [see Barlin & Benbow, *J. Chem. Soc.*, Perkin II, 1385 (1925)].

Therefore, as evidenced above, it is well established that both electrophilic and nucleophilic substitution are much more readily and practically performed on the quaternary salts of such pyridine and bipyridine bases. In this regard, the prior art above indicates that such quaternary salts are generally formed by the addition or substitution of a methyl or other alkyl group on the 1-position of the pyridine ring.

It has also long been known that quaternary salts of certain pyridine bases yield bipyridinium salts through coupling reactions upon treatment with a reducing reagent followed by an oxidizing reagent. In a like fashion, the quaternary salts of 4-cyanopyridines yield bipyridinium salts on treatment with sodium dithionite followed by either oxygen or iodine. See Kosower and Cotter, *J. Amer. Chem. Soc.*, 86 5524 (1964); Winters, Smith and Cohen, *J. Chem. Comm.*, 642 (1970).

A major problem experienced with the use of quaternary salts to achieve coupling or electrophilic or nucleophilic substitution is that of regeneration of the free pyridine or bipyridine base following the transformation reaction. The methods previously workable for ammonium salts have proven totally unsatisfactory in this regard; and until recently, no general methods have existed for the dealkylation of the quaternary salts of pyridine and its bases, as discussed above.

However, soft nucleophiles such as triphenylphosphine (PPh₃) and dimethylformamide (DMF) have now been reported to dealkylate the methyl quats of certain pyridine bases. See T. L. Ho, *Synth. Commun.*, vol. 3, 99 (1973); Aumann & Deady, *J. Chem. Soc. Chem. Commun.*, 32 (1973). Such reagents have been used both separately, as documented in Kutney and Greenhouse, *Synth. Commun.*, v. 5(2), 119-24 (1975) and Aumann & Deady, supra, and in combination, as reported in Berg, Gallow, & Metzger, *J. Org. Chem.*, vol. 41, 2821 (1976). In addition, T. L. Ho reported in his article, supra, the dealkylation of a pyridinium methiodide salt by refluxing the quaternary salt in DMF combined with 1,4-Diazabicyclo[2.2.2.] octane.

All of these prior art methods, or processes, for the dealkylation of quaternary pyridinium salts have major disadvantages both in their yields and costs of operation. In the case of triphenylphosphine, the reagent is converted to the salt, $CH_3-PPh_3I$, making recovery of the reagent very difficult and expensive at best. The DMF methods, on the other hand, give low yields or require long reaction times, as evidenced in the Aumann & Deady article, supra, thus making the methods impractical for commercial use. Also, the end products of the reaction are not readily recyclable.

A further known quaternary salt, in contrast to the methyl and other alkyl salts discussed above, is the pyridylethyl quaternary salt prepared by the method disclosed in the Cislak patent, U.S. Pat. No. 2,512,789. Cislak also worked with dipyridyl, or bipyridyl, quaternary salts as disclosed in his later patent, U.S. Pat. No. 3,049,547. While his patents state that the preparation of monochloride salts occurs, it has been subsequently learned that the relevant examples of the Cislak patents, if followed, actually produce the acid salt of the compounds formed (i.e., chloride hydrochloride compounds). Little work has been done with these pyridylethyl quaternary salts, however, and applicants are aware of no known process for their dequaternization.

Therefore, although quaternary salts provide important media for the electrophilic and nucleophilic substitution of various pyridine bases and for the coupling reactions to form bipyridine bases, their importance is substantially lessened by the fact that once formed, and the intermediate substitution steps completed, there has been no known process for simply and efficiently dequaternizing the salts to free the new substituted bases.

SUMMARY OF THE INVENTION

One embodiment of the present invention comprises a process for dequaternizing a 2-(2-pyridyl)ethyl or 2-(4-(pyridyl)ethyl quaternary salt or a pyridine or bipyridine base or its acid salt, comprising the step of reacting the pyridylethyl quaternary salt or its acid salt with a caustic material.

The above embodiment of the present invention constitutes a significant advance over the prior art because it provides a simple and easy process for dequaternizing the salt to yield the free pyridine or bipyridine base. In this way, a substituted pyridine base can be first quaternized to form the pyridylethyl salt in order to take advantage of the greater tendency of the salt to both couple and to undergo either electrophilic and nucleophilic substitution. When such intermediate reactions are completed, the new substituted pyridine or bipyridine base can then be freed by simply dequaternizing the salt in accordance with the present invention.

In one mode of practicing the above embodiment, the reacting step is accomplished by first combining the pyridylethyl quaternary salt with a caustic material, such as sodium hydroxide, and then causing the resultant mixture to be at a temperature sufficiently high and for such a length of time as to cause substantial dequaternization to occur. To optimize results, the desired temperature is between about 25° C. and about 150° C. and the causing step is for a period of about at least 1 hour and is sufficiently long to provide a yield of about at least 60%.

Other embodiments also contemplated within the present invention include processes for preparing a new pyridine or a bipyridine base from a first pyridine base via either a coupling reaction or an electrophilic or nucleophilic substitution reaction. In each of such embodiments, the process includes first selecting an appropriate 2-(2-pyridyl)ethyl or 2-(4-pyridyl)ethyl quaternary salt of a first pyridine base or its acid salt, mixing the salt with either an electrophile or nucleophile or with a reducing and oxidizing reagent, combining the resultant mixture with a caustic material and then causing the mixture to be at a temperature sufficiently high and for such a length of time as to cause substantial dequaternization to occur.

These other embodiments of the present invention also provide a significant advance over the prior art as previously discussed. Such processes provide the superior substitution and coupling properties inherent with quaternary salts while also providing a ready means for reversing the quaternization process to yield the free pyridine or bipyridine base after the intermediate reactions are completed.

One object of the present invention is to provide a new process for dequaternizing a 2-(2-pyridyl)ethyl or 2-(4-pyridyl)ethyl quaternary salt of a pyridine or bipyridine base that is simple and efficient and yields a high percentage of free base.

Another object of the present invention is to provide a new and improved process for preparing a second pyridine base from a first pyridine base via either electrophilic or nucleophilic substitution in which the pyridylethyl quaternary salt of the first base is formed, reacted and then dequaternized to yield the second free pyridine base.

A further object of the present invention is to provide a new and improved process for preparing a bipyridine base from a pyridine base in which the pyridylethyl quaternary salt of the pyridine base is first formed, coupled with itself and then dequaternized to yield the free bipyridine base.

Related objects and advantages of the present invention will become apparent from the following description.

DESCRIPTION OF THE PREFERRED EMBODIMENT

In accordance with the above discussion, one embodiment of the present invention comprises a process for dequaternizing a 2-(2-pyridyl)ethyl or 2-(4-pyridyl)ethyl quaternary salt of a pyridine or bipyridine base comprising the step of reacting the pyridylethyl quaternary salt with a caustic material. In this context, "pyridine or bipyridine base" is meant to include all substituted or unsubstituted pyridine and bipyridine homologs and derivatives which are operable in the claimed procedure. Also, "2-(2-pyridyl)ethyl or 2-(4-pyridyl)ethyl quaternary salt of a pyridine of bipyridine base" is meant to include all obtainable pyridylethyl quaternary salts of the same which are operable in the claimed procedure. Examples of such pyridine and bipyridine bases and their respective pyridylethyl quaternary salts are found in the several specific examples listed below.

"Caustic material" is meant to indicate a strong base such as an alkali hydroxide, with sodium hydroxide being the caustic of choice. The importance of this base material is that it be sufficiently basic to provide the impetus for dequaternizing the pyridylethyl salt and freeing the pyridine or bipyridine base. Expressed in other terms, the "caustic material" merely needs to be sufficiently alkaline to dequaternize the pyridylethyl salt to form the 2- or 4-vinylpyridine, as further discussed below.

The reacting step of the present embodiment further includes the dual steps of first combining the pyridylethyl quaternary salt with the caustic material and then causing the resultant mixture to be at a temperature sufficiently high and for such a length of time as to cause substantial dequaternization to occur. Although the specific temperature required depends in large part upon the specific pyridine or bipyridine base involved, experiments to date show the preferred temperature range to be between about 25° C. and about 150° C., with the most preferred temperature being about 100° C. The internal pressure can also vary preferably between about atmospheric and about 200 psi with any change in the pressure, of course, varying the required time and temperature to achieve dequaternization.

For industrial application, the causing step should be for a period of time sufficient to provide a yield of at least about 60% free pyridine or bipyridine base. Although highly variable, experiments to date show the period of time required to achieve such yields is between about 1 hour and about 10 hours depending, of course, upon the specific materials, the quantities involved and many other factors. In several experiments, it was even found that heating at about the preferred temperature for a period of only about 2 hours resulted in maximum yield, with further heating tending to cause polymerization and thus loss of the recyclable vinylpyridine freed during dequaternization. It has further been found advantageous to reflux the resultant mixture during the causing step; however, such is not required to achieve dequaternization.

The above process is suitable for use in either a batch or continuous operation with established principles and known equipment being suitable for use in either case. Isolation and recovery operations for the free pyridine or bipyridine base resulting from dequaternization can take many forms according to the particular salt involved. However, such operations can be performed with known equipment and processes; and the further recovery of 2- or 4-vinylpyridine formed during dequaternization can also be accomplished in like manner. This 2- or 4-vinylpyridine can then be often recycled to form additional pyridylethyl quaternary salts using, for example, the method of the Cislak U.S. Pat. Nos. 2,512,789 and 3,049,547. In this way, the entire process can be continuously repeated using the recovered 2- or 4-vinylpyridine to prepare more pyridylethyl quaternary salt as a preliminary step to each repeated cycle of the process. Material costs are thereby significantly lessened while the overall efficiency of the process is greatly increased.

Three other embodiments, or types, of the present invention as mentioned above also require the initial selection from a given class or group of 2-(2- pyridyl)ethyl or 2-(4-pyridyl)ethyl quaternary salts. Such pyridylethyl quaternary salts are known in the art; and in each case, the desired salt can be readily prepared by known prior art processes. In this regard, the Cislak patents, U.S. Pat. Nos. 2,512,789 and 3,049,547 disclose the accepted method of preparing pyridylethyl salts and the same are hereby expressly incorporated herein by reference for such purpose.

In brief summary, the Cislak formation process involves reacting a 2- or 4-vinylpyridine with a particular pyridine salt. The pyridine salt was in turn either previously or simultaneously prepared by reacting a pyridine or bipyridine base with a strong inorganic acid such as HSCN, sulfuric, HCl, HBr, HI, or phosphoric acid. This does not preclude the possible use of a very strong organic acid such as trichloroacetic or picric acid; however, no data is available currently on the use of such acids. The reaction temperature during the 2-(2-pyridyl)ethyl or 2-(4-pyridyl)ethyl quaternary salt formation may vary substantially from about room temperature to about 150° C. with the preferred temperature range apparently being between about 40° C. and about 100° C. In addition, although not required, it is advantageous to carry out the formation reaction in the presence of an organic solvent such as isopropanol. As previously mentioned, while Cislak discloses the formation of monochloride salts during quaternization, it appears that the corresponding acid salts are actually prepared. Such acid salts are, of course, readily reducible to their monochloride salts by simple neutralization.

With this in mind, a second embodiment of the present invention, hereinafter referred to as the Type 1 reaction, first involves the selection of a 2-(2-pyridyl)ethyl or 2-(4-pyridyl)ethyl quaternary salt of a first pyridine base having the formula

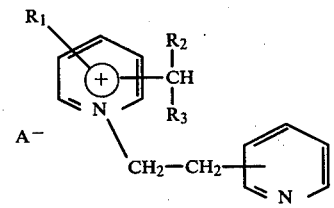

wherein A is an anion and $R_1$, $R_2$ and $R_3$ are hydrogen or an alkyl, aryl or arylalkyl group consisting of a branched or unbranched chain having from 1 to about 10 carbon atoms or a combination thereof, $R_1$ being located at any available position on the pyridine ring and

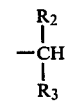

being located at the 2- or 4-position. Specific examples of quaternary salts falling within this class or type are contained in the specific examples, Nos. 13, 14, 15, 18, 19, 20 and 21 listed below.

The selected pyridylethyl quaternary salt is next mixed with an electrophile being sufficiently electrophilic to condense with the alpha carbon atom on the

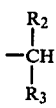

side chain in the presence of an appropriate mild organic base catalyst as is known in the prior art, such as a secondary or tertiary aliphatic amine as shown in specific example No. 13. In this regard, besides those electrophiles specifically listed in the examples hereinbelow, other workable electrophiles include acid chlorides, aldehydes, alkylhalides, and isocyanates. By analogy and argument with regard to other known literature, acceptable electrophiles for Type 1 reactions should also include ketones, esters, acid anhydrides, alkylnitriles, and arylhalides and olefins.

After the substitution or condensation reaction occurs, the resultant mixture is then combined with a caustic material as defined above, such as sodium hydroxide, and the mixture is caused to be at a temperature sufficiently high and for such a length of time as to cause substantial (over 60%) dequaternization to occur. In this regard, the temperature range and other specific variables associated with the combining and causing steps in the Type 1 reaction are identical with those already discussed hereinabove with regard to the first embodiment. Isolating and recovery operations would also be similar.

A third embodiment of the present invention, hereinafter referred to as the Type 2 reaction, concerns the preparation of a second pyridine base from a first base via nucleophilic substitution. First, a 2-(2-pyridyl)ethyl or 2-(4-pyridyl)ethyl quaternary salt of a first pyridine base is selected having the formula

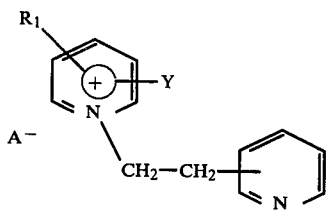

wherein:
(1) A is an anion;
(2) $R_1$ is as described above for the Type 1 reaction; and
(3) Y is hydrogen, cyanide or a halogen or an alkoxide, aryloxide, thioalkoxide or thioaryloxide having from 1 to about 10 carbon atoms or a primary amine or a secondary or tertiary amino group of the formula $-NR_2R_3$ wherein $R_2$ abd $R_3$ are as described above for the Type 1 reaction, Y being located at the 2- or 4-position on the pyridine ring.

The selected pyridylethyl quaternary salt from the above group is then mixed with a nucleophile being sufficiently nucleophilic to displace the Y substituent. In this regard, nucleophilicity data for many compounds and reagents are known in the art and readily available to assist in selecting an appropriate nucleophile for mixing with the selected pyridylethyl quaternary salt. Examples of specific nucleophile Y combinations are found in examples Nos. 1, 2, 3, 4, 5, 6–11 and 12 listed below.

A caustic material as defined above is also combined with the selected quaternary salt and the resultant mixture is then caused to be at a temperature sufficiently high and for such a length of time as to cause substantial (at least about 60%) dequaternization to occur. As with the Type 1 reaction, the characteristic temperature range and other variables used in the combining and causing steps are identical to those above described with regard to the first embodiment of the present invention and therefore need not be repeated.

Unlike the Type 1 reaction, however, the Type 2 reaction does not require the caustic material to be added to the mixture only after the nucleophilic substitution or displacement has occurred. Experiments to date indicate that at least in certain cases, the nucleophilic substitution or displacement reaction proceeds at such a rate that simultaneous addition of both the nucleophile and the caustic is possible. In this regard, it is well known that unlike the electrophile in the Type 1 reaction, the nucleophile is unaffected by contact with the caustic either prior to or after their addition. Nevertheless, it is still preferred to combine the caustic with the mixture after complete nucleophilic substitution has occurred in order to assure the purity of the free dequaternized pyridine base.

A fourth embodiment of the present invention, hereinafter referred to as the Type 3 reaction, concerns the preparation of a bipyridine base from a first pyridine base. Similar to the Type 2 reaction, the first step is selecting a 2-(2-pyridyl)ethyl or 2-(4-pyridyl)ethyl quaternary salt of a pyridine base having the formula

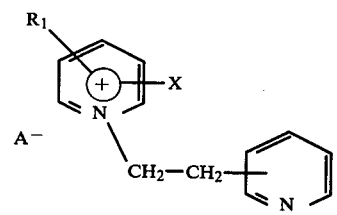

wherein $R_1$ and A are as defined above and X is cyanide or hydrogen, X being located at the 2- or 4-position on the pyridine ring, X being hydrogen when located at the 2-position (this occurring when $R_1$ is at the 4-position). Specific examples of two salts within this type are found in the examples Nos. 16 and 17 listed below.

The selected quaternary salt is next mixed in excess with a reducing and then an oxidizing reagent. Such redox reagent pair must be sufficiently strong to cause the bipyridyl quaternary salt to form. Experiments have shown that when X is a cyano group, a reducing reagent such as sodium dithionite is proper with air providing a suitable oxidizing reagent to complete the bipyridyl salt formation. When X is hydrogen, on the other hand, the coupling reaction to be carried out preferably uses a stronger reducing reagent such as either a reducing metal, such as sodium, or an alkali metal cyanide, such as sodium cyanide, with air again providing an oxidizing reagent.

As with both the Type 1 and Type 2 reactions, a caustic material such as sodium hydroxide is also added or combined and the resultant mixture then caused to be at a temperature sufficiently high and for such a length of time as to cause substantial (at least about 60%) dequaternization to occur thereby yielding the free bipyridine base.

In this regard, the Type 3 coupling reaction apparently sides with the Type 2 reaction as to when the caustic may be added, it being at least theoretically possible to simultaneously add the caustic along with the oxidizing reagent after the reducing reagent has been first added. As before, however, it is preferred to combine the caustic material with the resultant mixture after the redox reagent pair have been added and the coupling completed. Once again, the suitable temperature range, period of reaction and other variables required for the dequaternization portion of the Type 3 reaction are identical to those previously described with regard to the first embodiment of the present invention.

For the purposes of promoting a better understanding of the processes of the present invention, reference will be now be made to specific examples of the preparation of various 2-(2-pyridyl)ethyl and 2-(4-pyridyl)ethyl quaternary salts of pyridine and bipyridine bases and their subsequent dequaternization to yield the corresponding newly formed pyridine or bipyridine base and the re-formed 2- or 4-vinylpyridine compound.

EXAMPLE 1

To 166.4 parts of 4-cyanopyridine in 500 cc of isopropanol was added 170 parts of a 15.9% solution of hydrogen chloride in isopropanol. To this was added 292 parts of 2-vinylpyridine in 500 cc of isopropanol, and the resulting mixture heated to reflux for 5.5 hours. The reaction was cooled to 25° C. and 261 parts of 1-[2-(2-pyridyl)ethyl]-4-cyanopyridinium chloride hydrochloride isolated on filtration.

To 28.1 parts of this 1-[2-(2-pyridyl)ethyl]-4-cyanopyridinium chloride hydrochloride in 150 parts water was added 24 parts of piperidine, and the resulting mixture stirred for 2.5 hours at ambient temperature. 300 parts of 40% sodium hydroxide was added, and the reaction heated to 100° C. for two hours, cooled, and the organic layer separated. Distillation of the organic layer gave 15 parts 4-piperidinopyridine and 10 parts 2-vinylpyridine which was subsequently recycled for use in preparing more pyridylethyl salts.

EXAMPLE 2

To 28 parts of 1-[2-(2-pyridyl)ethyl]-4-cyanopyridinium chloride hydrochloride obtained as in Example 1, was added 30 parts water and 28 parts of a 32% aqueous dimethylamine solution. This solution was stirred for two hours, 200 parts 40% sodium hydroxide solution added, and the mixture boiled at reflux for two hours. Separation of layers and distillation gave 10.4 parts 4-dimethylaminopyridine with 10 parts 2-vinylpyridine being recovered and later recycled.

EXAMPLE 3

To 14 parts of the 4-cyanopyridinium quaternary acid salt obtained as in Example 1 was added 50 parts water and 12 parts diethanolamine, and the solution stirred for two hours at room temperature. 150 parts of 40% sodium hydroxide was added and boiled at refux for 1.5 hours. The mixture was cooled to 30° C. and extracted with 200 parts chloroform. Distillation of the chloroform extract gave 5.5 parts 4-diethanolaminopyridine.

EXAMPLE 4

To 28 parts of the preformed 4-cyanopyridinium quaternary acid salt was added 20 parts of sodium methoxide in 100 parts methanol. The resulting solution was stirred for five hours at 25° C., then boiled under reflux for four hours. The methanol was removed by distillation, and the residue extracted with 100 parts chloroform. Distillation of the chloroform gave 5.4 parts 4-methoxypyridine.

EXAMPLE 5

To 28 parts of the 4-cyanopyridinium quaternary salt as in Example 1, the acid salt having been removed by simple neutralization with sodium carbonate, was added 65 parts water and 100 parts concentrated ammonium hydroxide, the mixture stirred for two hours at 25° C. 150 parts of 40% sodium hydroxide was added and boiled at reflux for two hours. The resulting solution was extracted with 150 parts 2-butanol. Distillation of the extract gave 5.2 parts 4-aminopyridine.

EXAMPLES 6–11

The reaction as in Example 5 was carried out using hydrazine, monomethylamine, cyclohexylamine, allylamine, benzylamine, and furfurylamine to give the corresponding substituted 4-aminopyridine.

EXAMPLE 12

To 31.5 parts 4-cyanopyridine was added 25 parts water, 44 parts concentrated hydrochloric acid, and 21 parts 2-vinylpyridine. The mixture was heated to 60° C. for six hours, cooled to 30° C., and 36.5 parts of a 32% aqueous solution of dimethylamine added. After stirring two hours at 30° C., 200 parts of 40% sodium hydroxide was added, and the mixture boiled under reflux for two hours. The solution was cooled, the organic layer separated, and distilled to give 36.9 parts 4-dimethylaminopyridine with 21 parts 2-vinylpyridine being recovered.

EXAMPLE 13

To 140 parts 4-picoline, also commonly called 4-methylpyridine, was added 540 parts of a 21.5% solution of hydrogen chloride in isopropanol, then 236 parts 2-vinylpyridine was added, and the resultant solution heated to 90° C. for 16 hours. The mixture was cooled to 30° C. and filtered to give 300 parts 1-[2-(2-pyridyl)ethyl]-4-picolinium chloride hydrochloride.

To 135 parts of the 4-picolinium quaternary acid salt in 150 parts isopropanol was added 159 parts acrylonitrile and 56.5 parts 1-ethylpiperidine, and the resultant solution boiled at reflux for 3.5 hours. To the hot solution was added 230 parts 20% sodium hydroxide solution and the heating continued two hours. After the heating period, the solution was cooled to 30° C., the pH adjusted to 3.2 with hydrochloric acid, and the solid so formed was isolated to give 49.5 parts 4-[tris(2-carboxyethyl)-methyl]pyridine.

EXAMPLE 14

To 67.5 parts of the 4-picolinium quaternary salt as in Example 13 but without the acid salt was added 100 parts isopropanol, 32.5 parts benzaldehyde, and one part piperidine. The resulting solution was boiled at reflux two hours, 100 parts 40% sodium hydroxide added, and the heating continued for two hours. The cooled mixture was extracted with chloroform, and the organic phase evaporated to dryness to yield a residue that was recrystallized from methanol-water to give 21 parts 4-styrylpyridine.

EXAMPLE 15

To 67.5 parts of the quaternary salt of 2-picoline, also called 2-methylpyridine, (obtained as in Example 13) was added 100 parts methanol, one part piperidine, and 37 parts benzaldehyde. The solution was boiled at reflux for three hours, 175 parts 40% sodium hydroxide solution was added, and the heating continued 1.5 hour to give on workup, as in Example 13, 27 parts 2-styrylpyridine.

EXAMPLE 16

28 parts of the quaternary salt of 4-cyanopyridine (obtained as in Example 1) in 200 parts water was treated with 17.4 grams sodium dithionite and stirred at room temperature for two hours. Air was introduced into the solution at a rate of 20 cc/minute for two hours. To this solution was added 150 parts of 40% sodium hydroxide, and the solution boiled at reflux for two hours. The layers were separated. The organic layer contained 6.4 parts 4,4'-bipyridine.

EXAMPLE 17

To 22 parts of 1-[2-pyridyl)ethyl] pyridinium chloride (obtained from pyridine and 2-vinylpyridine as in Example 13) in 100 parts of a mixture of water-acetone (1:1 v/v) was added five parts sodium cyanide, and the mixture stirred 24 hours at 25° C. The resulting dark blue solution was oxidized with an alcoholic iodine solution until the blue color disappeared and 100 parts 40% sodium hydroxide added. Cleavage of the quat and workup as in Example 15 gave 4.9 parts 4,4'-bipyridine.

EXAMPLE 18

To 70 parts of 4-picoline, also called 4-methylpyridine, was added 270 parts of a 21.5% solution of hydrogen choride in isopropanol, then 118 parts 4-vinylpyridine was added and the resulting solution heated to 60° C. for 10 hours. The mixture was cooled to 30° C. and filtered to give 148 parts 1-[2-(4-pyridyl)ethyl]-4-picolinium chloride hydrochloride. The 1-[2-(4-pyridyl)ethyl]-4-picolinium chloride hydrochloride was then reacted with acrylontrile as in Example 13 to give 4-[tris(2-carboxyethyl)methyl]pyridine.

EXAMPLE 19

The reaction as in Example 13 was carried out using 1-[2-(2-pyridyl)ethyl]-4-n-propylpyridinium chloride and acrylonitrile.

EXAMPLE 20

The reaction as in Example 13 was carried out using the pyridylethyl quaternary salt of 4-picoline, also called 4-methylpyridine, with methyl benzoate as the electrophile to give beta-(4-pyridyl)-acetophenone.

EXAMPLE 21

The reaction as in Example 13 was carried out where the quaternary salt was 1-[2-(2-pyridyl)ethyl]-2-methylpyridinium chloride and the electrophile was acetic anhydride to give 2-acetonylpyridine.

What is claimed is:

1. A process for dequaternizing a 2-(2-pyridyl)ethyl or 2-(4-pyridyl)ethyl quaternary salt of a pyridine or bipyridine base or its acid salt, comprising the step of reacting the pyridylethyl quaternary salt or its acid salt with a caustic material.

2. The process in claim 1 additionally comprising recovering the 2- or 4-vinylpyridine formed during said reacting.

3. The process in claim 2 additionally comprising repeating the process using the recovered 2- or 4-vinylpyridine to prepare the pyridylethyl quaternary salt.

4. The process in claim 1 in which said reacting is in the presence of an organic solvent.

5. The process in claim 4 in which the organic solvent is isopropanol.

6. The process in claim 1 in which said reacting includes:
   (a) combining the pyridylethyl quaternary salt with the caustic material; and
   (b) causing the resultant mixture to be at a temperature sufficiently high and for such a length of time as to cause substantial dequaternization to occur.

7. The process in claim 6 in which said combining is with sodium hydroxide.

8. The process in claim 6 in which the pyridylethyl quaternary salt or its acid salt is of a pyridine base from the group consisting of
4-piperidinopyridine;
4-dimethylaminopyridine;
4-methoxypyridine;
4-aminopyridine;
4-[tris(2-carboxyethyl)methyl]pyridine;
4-styrylpyridine;
2-styrylpyridine;
4-diethanolaminopyridine; and
2-acetonylpyridine.

9. The process in claim 8 in which the pyridylethyl quaternary salt or its acid salt is of 4-dimethylaminopyridine.

10. The process of claim 8 in which the quaternary salt is a chloride or a chloride hydrochloride.

11. The process in claim 6 in which the pyridylethyl quaternary salt or its acid salt is of a bipyridine base from the group consisting of
4,4'-bipyridine;
2,2'-bipyridine;
2,2'-dimethyl-4,4'-bipyridine; and
3,3'-dimethyl-4,4'-bipyridine.

12. The process of claim 11 in which the quaternary salt is a chloride or a chloride hydrochloride.

13. The process in claim 6 in which said causing is for a period of time sufficient to provide a yield of at least about 60%.

14. The process in claim 6 in which said causing is to a temperature of between about 25° C. and about 150° C.

15. The process in claim 14 in which said combining is with sodium hydroxide.

16. The process in claim 15 in which said causing is for a period of about at least 1 hour and to a temperature of about 100° C.

17. The process in claim 16 additionally comprising recovering the dequaternized pyridine or bipyridine base formed during said causing.

18. The process in claim 17 additionally comprising recovering the 2- or 4-vinylpyridine formed during said causing.

19. The process in claim 18 additionally comprising repeating the process using the recovered 2- or 4-vinylpyridine to prepare the pyridylethyl quaternary salt.

20. A process for preparing a second pyridine base from a first pyridine base via electrophilic substitution, comprising the steps of:
   (a) selecting a 2-(2-pyridyl)ethyl or 2-(4-pyridyl)ethyl quaternary salt of a first pyridine base having the formula

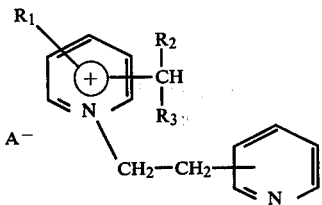

or its acid salt, wherein A is an anion and $R_1$, $R_2$ and $R_3$ are hydrogen or an alkyl, aryl or arylalkyl group consisting of a branched or unbranched chain having from 1 to about 10 carbon atoms or a combination thereof, $R_1$ being located at any available position on the pyridine ring and

being located at the 2- or 4-position;
- (b) mixing an electrophile with the selected quaternary salt or its acid salt in the presence of a mild organic base catalyst, the electrophile being sufficiently electrophilic to condense with the alpha carbon atom on the

substituent;
- (c) after the condensation has occurred, combining the resultant mixture with a caustic material; and
- (d) causing the resultant mixture to be at a temperature sufficiently high and for such a length of time as to cause substantial dequaternization to occur.

21. The process in claim 20 additionally comprising recovering the 2- or 4-vinylpyridine formed during said causing.

22. The process in claim 21 additionally comprising repeating the process using the recovered 2- or 4-vinylpyridine to prepare the pyridylethyl quaternary salt.

23. The process in claim 20 in which said reacting is in the presence of an organic solvent.

24. The process in claim 23 in which the organic solvent is isopropanol.

25. The process in claim 20 in which the mild organic base catalyst is 1-ethylpiperidine.

26. The process in claim 20 in which the selected quaternary salt or its acid salt is of a first pyridine base from the group consisting of
4-methylpyridine;
4-ethylpyridine;
4-benzylpyridine;
4-n-propylpyridine;
4-(5-nonyl)pyridine;
2-methylpyridine;
2-ethylpyridine;
2-benzylpyridine; and
5-ethyl-2-methylpyridine.

27. The process in claim 26 in which the quaternary salt is a chloride or a chloride hydrochloride.

28. The process in claim 20 in which said mixing is with an electrophile from the group consisting of
acrylonitrile;
methyl benzoate;
benzaldehyde;
acetic anhydride;
phenyl isocyanate;
isopropyl bromide;
benzoyl chloride;
acetoacetic ester; and
methyl acrylate.

29. The process in claim 20 in which said combining is with sodium hydroxide.

30. The process in claim 20 in which said causing is to a temperature of between about 25° C. and about 150° C.

31. The process in claim 30 in which said causing is for a period of time sufficient to provide a yield of at least about 60%.

32. The process in claim 31 in which said causing is for a period of at least about 1 hour and to a temperature of about 100° C.

33. The process in claim 32 in which said combining is with sodium hydroxide.

34. The process in claim 33 additionally comprising recovering the dequaternized pyridine base formed during said causing.

35. The process in claim 34 additionally comprising recovering the 2- or 4-vinylpyridine formed during said causing.

36. The process in claim 35 additionally comprising repeating the process using the recovered 2- or 4-vinylpyridine to prepare the pyridylethyl quaternary salt.

37. The process in claim 31 in which said selecting is of 1-[2-(2-pyridyl)ethyl]-4-methylpyridinium chloride and said mixing is with acrylonitrile.

38. The process in claim 31 in which said selecting is of 1-[2-(2-pyridyl)ethyl]-4-n-propylpyridinium chloride and said mixing is with acrylonitrile.

39. The process in claim 31 in which said selecting is of 1-[2-(2-pyridyl)ethyl]-4-methylpyridinium chloride and said mixing is with methylbenzoate.

40. The process in claim 31 in which said selecting is of 1-[2-(2-pyridyl)ethyl]-2-methylpyridinium chloride and said mixing is with acetic anhydride.

41. A process for preparing a second pyridine base from a first pyridine base via nucleophilic substitution, comprising the steps of:
- (a) selecting a 2-(2-pyridyl)ethyl or 2-(4-pyridyl)ethyl quaternary salt of a first pyridine base having the formula

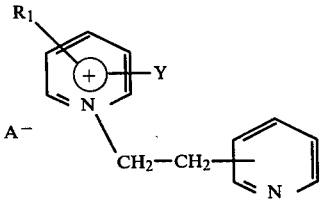

or its acid salt, wherein:
- (1) A is an anion;
- (2) Y is hydrogen, cyanide or a halogen or an alkoxide, aryloxide, thioalkoxide or thioaryloxide having from 1 to about 10 carbon atoms or a primary amine or a secondary or tertiary amino group of the formula —NR$_3$R$_3$, Y being located at the 2- or 4-position on the pyridine ring; and (3) R$_1$, R$_2$ and R$_3$ are hydrogen or a lower alkyl, aryl or arylalkyl group consisting of a branched or unbranched chain having from 1 to about 10 carbon atoms or a combination thereof, R$_1$ being located at any available position on the pyridine ring;

(b) mixing a nucleophile with the selected quaternary salt or its acid salt, the nucleophile being sufficiently nucleophilic to displace the Y substituent;

(c) combining a caustic material with the nucleophile and the selected quaternary salt or its acid salt; and (d) causing the resultant mixture to be at a temperature sufficiently high and for such a length of time as to cause substantial dequaternization to occur.

42. The process in claim 41 in which said selecting is of 1-[2-(2-pyridyl)ethyl]-4-cyanopyridinium chloride and said mixing is with dimethylamine.

43. The process in claim 41 additionally comprising recovering the 2- or 4-vinylpyridine formed during said causing.

44. The process in claim 43 additionally comprising repeating the process using the recovered 2- or 4-vinylpyridine to prepare the pyridylethyl quaternary salt.

45. The process in claim 41 in which said reacting is in the presence of an organic solvent.

46. The process in claim 45 in which the organic solvent is isopropanol.

47. The process in claim 41 in which said combining is after the displacement has occurred.

48. The process in claim 47 in which the selected quaternary salt or its acid salt is of a first pyridine base from the group consisting of
4-cyanopyridine;
2-methyl-4-cyanopyridine;
2-cyanopyridine;
pyridine; and
2-chloropyridine.

49. The process in claim 48 in which the quaternary salt is a chloride or a chloride hydrochloride.

50. The process in claim 47 in which said combining is with sodium hydroxide.

51. The process in claim 47 in which said causing is to a temperature of between about 25° C. and about 150° C.

52. The process in claim 51 in which said causing is for a period of time sufficient to provide a yield of at least about 80%.

53. The process in claim 52 in which said causing is for a period of at least about 1 hour and to a temperature of about 100° C.

54. The process in claim 53 in which said combining is with sodium hydroxide.

55. The process in claim 54 additionally comprising recovering the dequaternized pyridine base formed during said causing.

56. The process in claim 52 additionally comprising recovering the 2- or 4-vinylpyridine formed during said causing.

57. The process in claim 56 additionally comprising repeating the process using the recovered 2- or 4-vinylpyridine to prepare the pyridylethyl quaternary salt.

58. The process in claim 52 in which the selected quaternary salt is 1-[2-(2-pyridyl)ethyl]-4- cyanopyridinium chloride hydrochloride and the nucleophile is from the group consisting of
dimethylamine;
piperidine;
ammonia;
diethanolamine; and
sodium methoxide.

59. The process in claim 52 in which the selected quaternary salt is 1-[2-(2-pyridyl)ethyl]-2-cyanopyridinium chloride and the nucleophile is from the group consisting of
dimethylamine;
piperidine;
diethanolamine; and
sodium methoxide.

60. A process for preparing a 2,2'- or 4,4'-bipyridine base from a first pyridine base, comprising the steps of:

(a) selecting a 2-(2-pyridyl)ethyl or 2-(4-pyridyl)ethyl quaternary salt of a first pyridine base having the formula

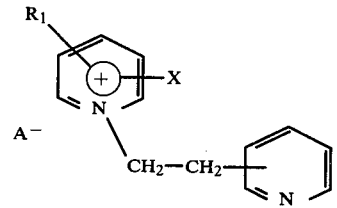

or its acid salt, wherein:
(1) A is an anion;
(2) R$_1$ is hydrogen or a lower alkyl, aryl or arylalkyl group consisting of a branched or unbranched chain having from 1 to about 10 atoms, R$_1$ being located at any available position on the pyridine ring; and
(3) X is cyanide or hydrogen, X being located at the 2- or 4-position, X being hydrogen when located at the 2-position;

(b) mixing the selected quaternary salt or its acid salt in excess with a reducing reagent and then an oxidizing reagent sufficiently strong to cause the bipyridyl quaternary salt to form;

(c) combining a caustic material with the reducing and oxidizing reagents and the pyridylethyl quaternary salt or its acid salt; and (d) causing the resultant mixture to be at a temperature sufficiently high and for such a length of time as to cause substantial dequaternization to occur.

61. The process in claim 60 additionally comprising recovering the 2- or 4-vinylpyridine formed during said causing.

62. The process in claim 61 additionally comprising repeating the process using the recovered 2- or 4-vinylpyridine to prepare the pyridylethyl quaternary salt.

63. The process in claim 60 in which said combining is after the coupling has occurred.

64. The process in claim 63 in which said reacting is in the presence of an organic solvent.

65. The process in claim 64 in which the organic solvent is isopropanol.

66. The process in claim 63 in which the selected quaternary salt or its acid salt is of a first pyridine base from the group consisting of
4-cyanopyridine;
pyridine;
3-methyl-4-cyanopyridine; and
3-methylpyridine.

67. The process in claim 66 in which the quaternary salt is a chloride or a chloride hydrochloride.

68. The process in claim 63 in which the selected quaternary salt or its acid is of a first pyridine base from the group consisting of
2-cyanopyridine;
pyridine; and
4-methylpyridine.

69. The process in claim 68 in which the quaternary salt is a chloride or a chloride hydrochloride.

70. The process in claim 63 in which said mixing is with a reducing reagent from the group consisting of sodium dithionite, a reducing metal and an alkali metal cyanide.

71. The process in claim 70 in which said mixing is with sodium dithionite when X is cyanide.

72. The process in claim 70 in which said mixing is with sodium or sodium cyanide when X is hydrogen.

73. The process in claim 70 in which the oxidizing reagent is air.

74. The process in claim 63 in which said causing is to a temperature of between about 25° C. and about 150° C.

75. The process in claim 74 in which said causing is for a period of time sufficient to provide a yield of at least about 60%.

76. The process in claim 75 in which said causing is for a period of about at least 1 hour and to a temperature of about 100° C.

77. The process in claim 76 in which said combining is with sodium hydroxide.

78. The process in claim 77 additionally comprising recovering the dequaternized bipyridine base formed during said causing.

79. The process in claim 78 additionally comprising recovering the 2- or 4-vinylpyridine formed during said causing.

80. The process in claim 79 additionally comprising repeating the process using the recovered 2- or 4-vinylpyridine to prepare the pyridylethyl quaternary salt.

81. The process in claim 75 in which said selecting is of 1-[2-(2-pyridyl)ethyl]-4-cyanopyridinium chloride or its hydrochloride and said mixing is with sodium dithionite and then air.

* * * * *